United States Patent [19]
Rowsey

[11] Patent Number: 5,584,881
[45] Date of Patent: Dec. 17, 1996

[54] SUTURELESS CORNEAL TRANSPLANTATION APPARATUS AND METHOD

[76] Inventor: J. James Rowsey, 1000 S. Harbor Island Blvd., #2605, Tampa, Fla. 33602

[21] Appl. No.: 289,670

[22] Filed: Aug. 12, 1994

[51] Int. Cl.$^6$ .................................................. A61F 2/14
[52] U.S. Cl. ............................................................ 623/5
[58] Field of Search ............................ 623/4, 5; 606/107, 606/166; 128/898

[56] References Cited

U.S. PATENT DOCUMENTS

| | | |
|---|---|---|
| 3,454,966 | 7/1969 | Rosen . |
| 3,945,054 | 3/1976 | Fedorov et al. . |
| 4,127,903 | 12/1978 | Schachar . |
| 4,190,050 | 2/1980 | Bailey . |
| 4,236,519 | 12/1980 | La Russa et al. . |
| 4,429,696 | 2/1984 | Hanna . |
| 4,563,779 | 1/1986 | Kelman ........................................ 623/5 |
| 4,612,012 | 9/1986 | White ........................................... 623/5 |
| 4,662,881 | 5/1987 | Nordan ......................................... 623/5 |
| 4,718,420 | 1/1988 | Lemp ......................................... 128/310 |
| 4,772,283 | 9/1988 | White ........................................... 623/5 |
| 4,810,082 | 3/1989 | Abel, Jr. ..................................... 351/160 |
| 4,824,066 | 4/1989 | Smith . |
| 4,842,599 | 6/1989 | Bronstein ..................................... 623/5 |
| 5,030,230 | 7/1991 | White ........................................... 623/5 |
| 5,139,518 | 8/1992 | White ........................................... 623/5 |

FOREIGN PATENT DOCUMENTS

| | | | |
|---|---|---|---|
| 9308878 | 5/1993 | WIPO | ..................................... 606/166 |

*Primary Examiner*—Mary Beth Jones
*Attorney, Agent, or Firm*—Dominik & Stein

[57] ABSTRACT

An eye with a cornea repaired without sutures comprising a donor material in the shape of a partial sphere having a generally central extent, the central extent being of the size and shape of the central portion of a cornea of an eye, the central extent having a periphery of a fixed diameter with an exterior surface in a convex configuration and an interior surface in a concave configuration and with an essentially common thickness throughout, the central extent having a plurality of corneal flaps extending radially from the periphery of the central extent, the flaps having exterior surfaces as a continuation of the exterior surface of the central extent; and a recipient eye in the shape of a partial sphere having a circular aperture in the cornea at its central portion, the central aperture being of a size and shape essentially that of the periphery of the central extent of the donor material, the aperture being of a common thickness at the periphery of the aperture, the central portion having pockets and with the central extent of the donor material located within the aperture of the recipient eye and with the flaps of the central extent being imbricated into the pockets of the recipient eye.

1 Claim, 3 Drawing Sheets

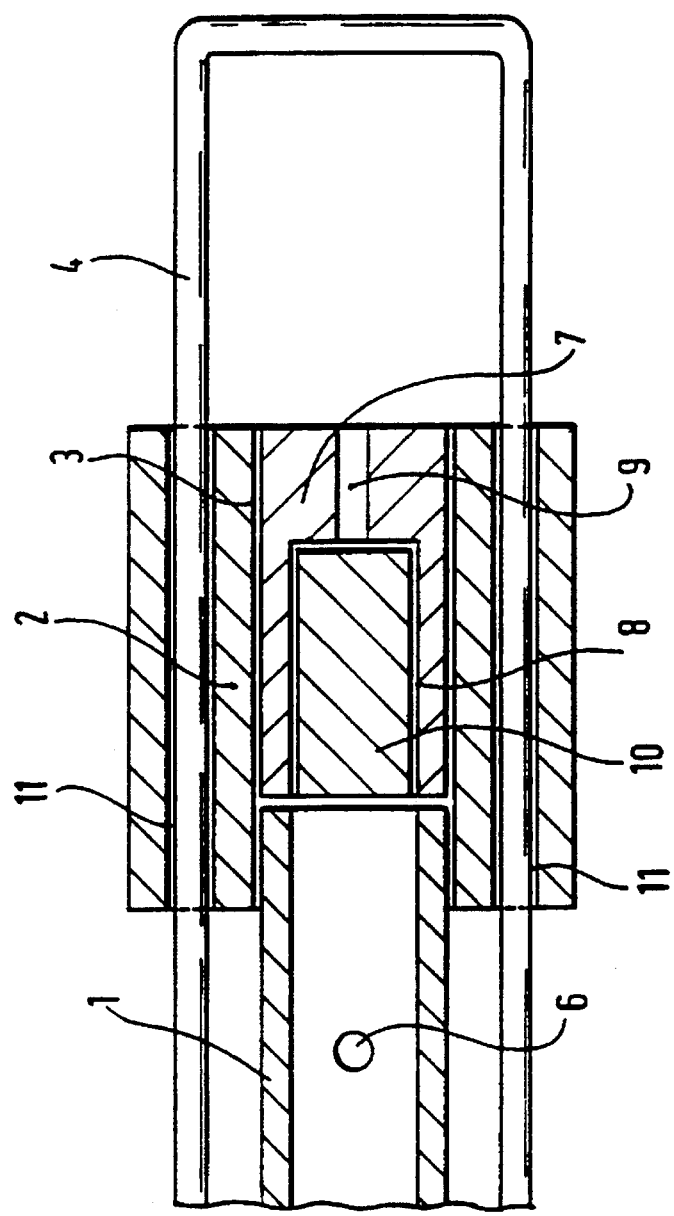

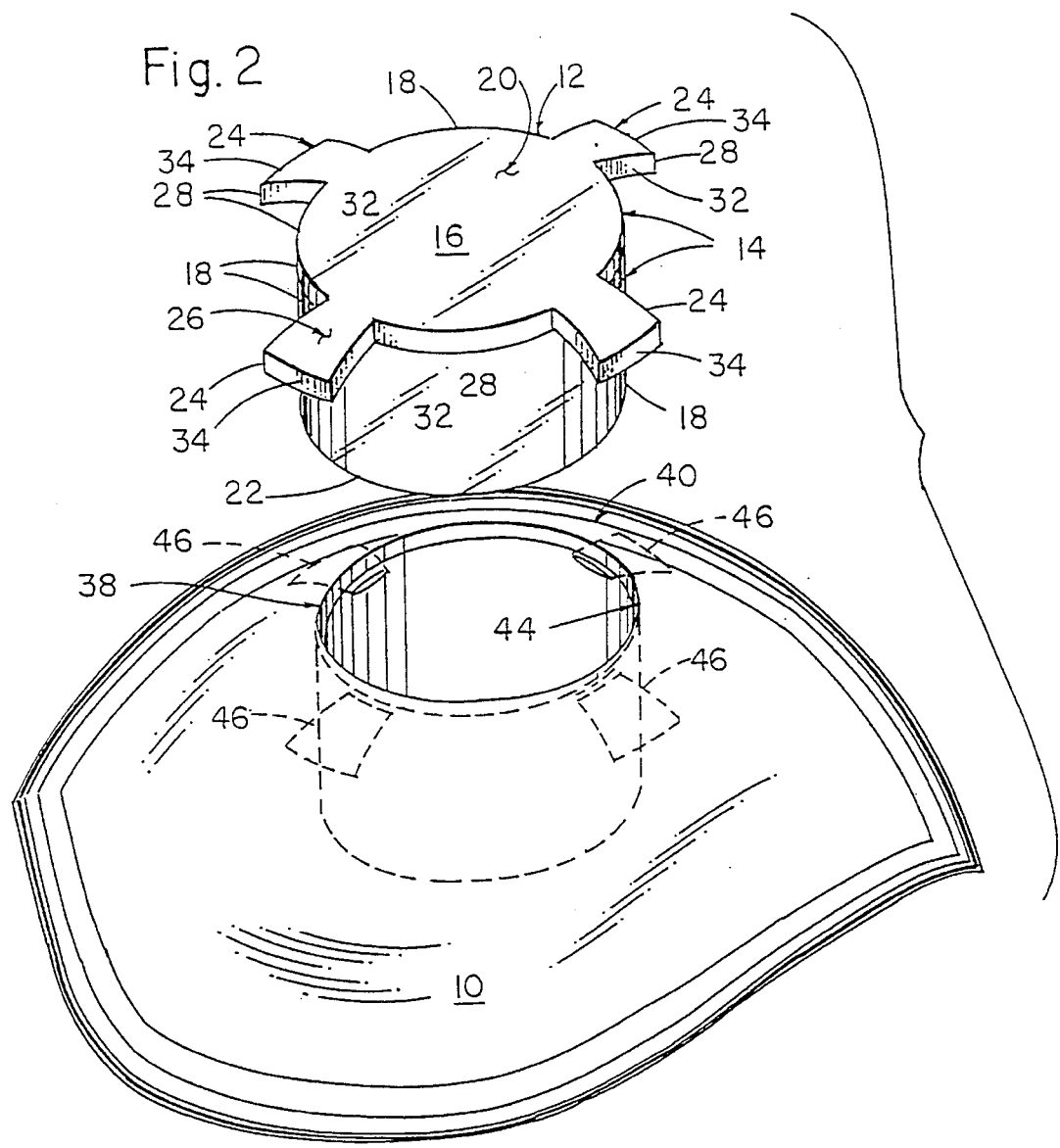

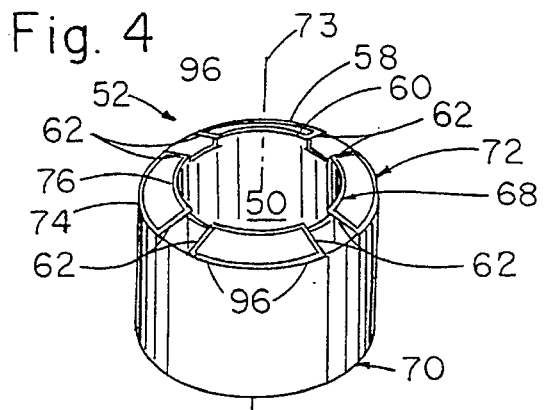
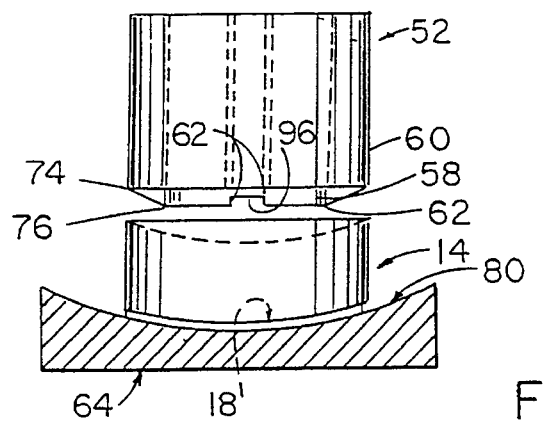
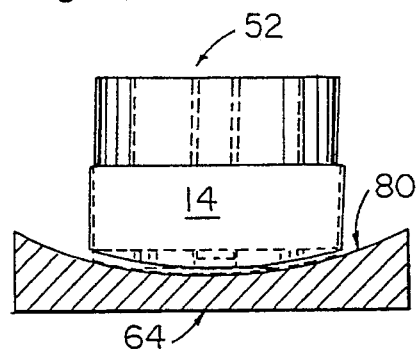
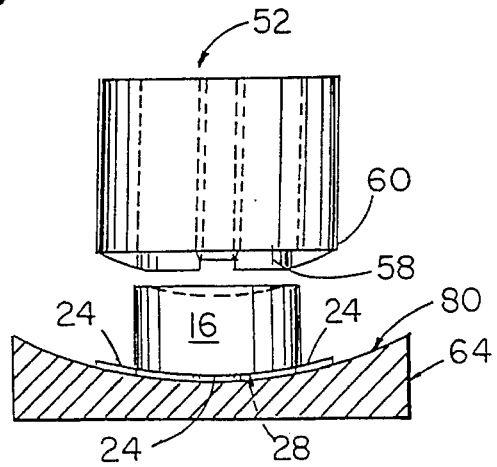

SUTURELESS CORNEAL TRANSPLANTATION APPARATUS AND METHOD

BACKGROUND OF THE INVENTION

1. Field of the Invention

This invention relates to sutureless corneal transplantation and, more particularly, to a method and apparatus for transplanting corneas without the use of sutures.

2. Description of the Background Art

Corneal transplantation occurs in approximately 37,000 patients in the United States per year. Each of these patients has delayed wound healing because of the avascular nature of the cornea. The stromal wound healing is facilitated by sutures. The sutures, however, induce astigmatism. The current trephine cutting techniques also produce tissue addition or tissue removal asymmetrically around the corneal periphery. These tissue aberrations further increase astigmatism.

Continuing efforts are being made to improve eye surgery methods and apparatus. Consider background patents which illustrate, for example, the large number of corneal transplant techniques such as in U.S. Pat. No. 3,945,054 to Fedorov and U.S. Pat. No. 4,772,283; 5,030,230 and 5,139,518 all to White.

In addition, apparatus including punches for preparing donor material for corneal transplants are disclosed in another large number of patents. By way of example, note U.S. Pat. No. 4,236,519 to La Russa; U.S. Pat. No. 4,824,066 to Smith; U.S. Pat. No. 4,718,420 to Lemp; U.S. Pat. No. 4,429,696 to Hanna; and U.S. Pat. No. 4,190,050 to Bailey.

Another grouping of background patents are those which disclose corneal layers used in association with eye surgery. By way of example, note U.S. Pat. No. 4,662,881 to Nordan; U.S. Pat. No. 3,454,966 to Rosen; and U.S. Pat. No. 4,810,082 to Abel.

Lastly, U.S. Pat. No. 4,127,903 to Schachar discloses an intraocular lens.

Efforts to improve eye surgery techniques continue. Accordingly, it is an object of this invention to provide an improvement which overcomes inadequacies of the prior art devices and provides an improvement which is a significant contribution to the advancement of the art.

Another object of this invention is to provide a new device that allows for penetrating keratoplasty with attendant corneal flaps.

A further object of the present invention is to use corneal flaps from the donor material into the recipient rim.

A further object of the present invention is to transplant corneas without sutures.

A further object of the present invention is a more rapid completion of a corneal transplant.

A further object of the present invention is reduced corneal astigmatism.

A further object of the present invention is to improve wound healing following corneal transplant.

A further object of the present invention is to reduce incidences of graft rejection following corneal transplants.

A further object of the present invention is to improve wound coaptation following corneal transplants.

A further object of the present invention is to transplant a cornea without sutures comprising (1) a donor material in the shape of a partial sphere having a central extent, the central extent being of the size and shape of the central portion of the cornea of the eye, the central extent having a periphery and an exterior surface in a convex configuration and an interior surface in a concave configuration and with an essentially common thickness throughout, the central extent having a plurality of corneal flaps extending radially from the periphery of the central extent, the flaps having exterior surfaces as a continuation of the exterior surface of the central extent and (2) a recipient eye in the shape of a partial sphere having an aperture in the cornea at its central portion, the aperture in the cornea being of a size and shape essentially that of the periphery of the central extent of the donor material, the central portion having pockets equal in number to the plurality of flaps of the donor material and aligned therewith, and with the central extent of the donor material located within the aperture of the recipient eye and with the flaps of the central extent being located within the respective pockets of the recipient eye.

The foregoing has outlined some of the pertinent objects of the invention. These objects should be construed to merely illustrative of some of the more prominent features and applications of the intended invention. Many other beneficial results can be attained by applying the disclosed invention in a different manner or modifying the invention within the scope of the disclosure. Accordingly, other objects and a fuller understanding of the invention and the detailed description of the preferred embodiment in addition to the scope of the invention defined by the claims taken in conjunction with the accompanying drawings.

SUMMARY OF THE INVENTION

For the purpose of summarizing this invention, this invention comprises an eye with a cornea repaired without sutures comprising, in combination, a donor material and a recipient eye. The donor material is in the shape of a partial sphere and is cut in a generally circular central extent, the central extent being of the size and shape of the central portion of a cornea of an eye, the central extent having a periphery of a fixed diameter of between about 7.0 and 7.5 millimeters with an exterior surface in a convex configuration and an interior surface in a concave configuration and with an essentially common thickness throughout, the central extent having four to eight, preferably six, symmetrically positioned corneal flaps, preferably diamond-shaped, extending radially from the periphery of the central extent, the flaps having exterior surfaces as a continuation of the exterior surface of the central extent, and the exterior surfaces of the central extent and the flaps being of a common Bowman's membrane of about 100 microns thickness. Preferably, the flaps have a thickness of about 10 percent of the thickness of the central extent with the area of juncture between the flaps and the central extent constituting between about 10 percent and 100 percent (i.e., one continuous flap) of the circumference of the central extent, with the radial dimension of each flap being between about 25 and 75 percent of the diameter of the central extent, with the side edges of the flaps being radii of the central extent, and with the radially exterior edge of each flap being curved concentric with the curvature of the central extent. The recipient eye is in the shape of a partial sphere having a circular aperture in the cornea at its central portion, the circular aperture being of a size and shape essentially that of the periphery of the central extent of the donor material, the aperture being of a common thickness at the periphery of the aperture, the central portion having four to eight, preferably six, symmetrically positioned pockets, with the pockets being at the area adjacent to the periphery of the aperture and constituting between about 10 percent and 100 percent (i.e., one continuous flap) of the periphery of the aperture, and with the radial dimension of each pocket being between about 25 and 75 percent of the diameter of the aperture. The central extent of the donor material is positioned within the aperture of the recipient eye, and then the flaps of the central extent are imbricated into the respective pockets of the recipient eye.

Advantageously, corneal transplantation according to this invention permits elevated intraocular pressure without tissue movement. Further, the imbrication of the flaps into the pockets reduces astigmatism in the postoperative period.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which:

FIG. 1 is a perspective illustration of the preferred embodiment of a sutureless corneal transplant effected in accordance with the principles of the present invention;

FIG. 2 is an exploded perspective view of the eye illustrated in FIG. 1;

FIG. 3 is a cross sectional view of the repaired eye of FIG. 1;

FIG. 3A is a cross-sectional view of the repaired eye of FIG. 1 but with the pockets in the recipient eye being positioned further interiorly;

FIG. 4 is a perspective illustration of a trephine for use in association with the sutureless corneal transplant technique of the present invention;

FIG. 5 is a side elevational view of the trephine of FIG. 4 and an associated block;

FIG. 6 is a side elevational view similar to FIG. 5 but showing the trephine during the cut; and FIG. 7 is a side elevational view similar to FIGS. 5 and 6 but showing the trephine in the retracted position after the cut.

Similar reference characters refer to similar parts throughout the several views of the drawings.

DETAILED DESCRIPTION OF THE PREFERRED EMBODIMENT

The present invention as illustrated in FIGS. 1 and 2 relates to an eye 10 with a cornea 12 repaired without sutures. The repaired cornea includes two major components, the donor material 14 and the recipient eye 10.

With regard to the donor material 14, such material is cut to a particular shape prior to being coupled with the recipient eye 10. The shape is that of a partial sphere. Such sphere has a generally circular central extent 16. The central extent 16 is of the size and shape of the central portion of the cornea of an eye. The central extent 16 has a periphery 18 of a fixed diameter of about 7.0 and 7.5 millimeters. It has an exterior surface 20 in a convex configuration. It also has an interior surface 22 in a concave configuration. The central extent 16 also has an essentially common thickness throughout.

Formed as part of the central extent are a plurality of symmetrically positioned diamond-shaped corneal flaps 24. Four to eight of such flaps is the preferred number and six is the most preferred. Such flaps 24 extend radially from the periphery 18 of the central extent 16. The flaps 24 have exterior surfaces 26 as a continuation of the exterior surface 20 of the central extent 16. The exterior surfaces 20 and 26 of the central extent 16 and flaps 24, respectively, are preferably of a common Bowman's membrane 28 typically having a thickness of about 100 microns.

The flaps 24 typically have a thickness of about 10 percent of the thickness of the central extent 16 of the donor material. The radial dimension of each flap 24 is between about 25 and 75 percent of the diameter of the central extent 16. The side edges 32 of the flaps 24 are preferably formed as radii of the central extent 16. In addition, the radially exterior edges 34 are preferably curved essentially concentric with the curvature of the central extent.

The next component of the repaired cornea is the recipient eye 10. Such eye 10 is in the shape of a partial sphere. The recipient eye 10 is formed with a circular central aperture 38 at its central portion 40. The circular central aperture 38 is of a size and shape essentially that of the periphery 18 of the central extent 16 of the donor material 14 for the receipt thereof. The periphery 42 of the aperture 38 is of a common thickness. The central portion 40 has a plurality (four illustrated) of symmetrically positioned pockets 46. The pockets 46 are simply incisions made into the thickness of the cornea, preferably just under the Bowman's membrane 28 into the periphery 42 of the aperture 38. The pockets 46 each constitute between about 10 and 100 percent of the periphery 42 of the aperture 38. The radial dimension of each pocket 46 is between about 25 and 75 percent of the diameter of the aperture 38.

In operation and use, the central extent 16 of the donor material 14 is positioned within the aperture 38 of the recipient eye 10. The flaps 24 of the central extent 16 are imbricated into the pockets 46 of the recipient eye 10. Forceps are preferably used for the positioning of the central extent and the imbrication of each of the flaps 24 into their respective pockets 46.

The present invention, in addition to the combination of the donor material 14 and recipient eye 10, also includes the method of repairing the recipient eye 10. Such method includes the step of providing donor material 14 of the type as described above. The method also includes the step of providing a recipient eye 10 as described above. The method then includes a step of positioning the donor material 14 with its central extent 16 within the aperture 38 of the recipient eye 10 and imbricating the flaps 24 of the donor material 14 into the pockets 46 of the recipient eye 10.

The invention further comprises a method for preparing the donor material 14 and for preparing the recipient eye 10. More particularly, the central extent 16 and the flaps 24 are preferably cut out of the donor material 14 obtained from a donor's eye (not shown). Such cuts are preferably made by first inverting the donor material 14 and resting its convex exterior surface 20 onto a suitable support and then holding it into position by means of vacuum or the like. The cuts are then made through the donor material 14 in an outline configuration to produce the central extent 16 with the plurality of flaps 24. Preferably, such cuts are made parallel to the axis of the partial sphere of the central extent 16. Additional cuts are then made at the juncture between the central extent 16 and the flaps 24 to a depth of about 90 percent of the thickness of the central extent 16, thereby leaving intact the common Bowman's membrane 48 of the central extent 16 and the flaps 24 that constitutes the convex exterior surfaces 20 and 26 of the central extent 16 and the flaps 24, respectively. Finally, additional cuts are made parallel along the Bowman's membrane 28 constituting the exterior surface 26 of the flaps 24 so as to remove the corneal material from the flaps 24 while leaving intact the Bowman's membrane 28 of the flaps 24 and the central extent 16.

The recipient eye 10 is prepared according to the method of this invention by first marking the intended location of the pockets 46 with a conventional corneal marking tool (not shown). The circular aperture 38 is then cut into the central portion 40 of the recipient eye 10 by means of a conventional trephine or the like which makes a circular cut through the central portion 40 whereupon the central portion 40 of the recipient eye 10 is removed and discarded. The pockets 46 are then formed into the periphery 42 of the central aperture 38 and the recipient eye 10 by means of a conventional diamond knife (not shown) having a width equal to the proximal width of the openings of the pockets 46 intended to be formed in the periphery 42 of the circular aperture 38. Each pocket 46 is then formed by inserting the diamond knife into the periphery 42 of the central aperture 38 of the recipient eye 10 in alignment with the respective corneal markings previously made. As shown in FIG. 3, the knife is preferably positioned just under the Bowman's membrane and then advanced inwardly to a depth equal to the intended depth of the pocket 46. The diamond knife is then moved in both directions sideways so as to cut a diamond-shaped pocket corresponding to the size and shape of the flaps 24. It is noted, however, that the width of the diamond knife and hence the width of the opening into the pockets 46 may be appreciably smaller than the corresponding width of the flaps 24 at its juncture with the central extent 16 so as to more securely retain the flaps 24 in the pockets 46.

After preparing the donor material 14 and the recipient eye 10 in the manner described above, the donor material 14 may then be coupled with the recipient eye 10 by positioning the central extent 16 of the donor material 14 into the central aperture 38 of the recipient eye 10. Each of the flaps 24 are imbricated into the respective pockets 46 by means of forceps which, when pressed upon each of the flaps 24, cause the flaps 24 to fold, thereby facilitating the insertion of the flaps 24 into their respective pockets 46. After all of the flaps 24 are positioned within their respective pockets 46, the central extent 16 is securely retained within the central aperture 38 of the recipient eye 10 in such a manner that postoperative astigmatism is minimized while permitting increased intraocular pressure without tissue movement.

It is noted that if the width of the openings of the pockets 46 were incised appreciably smaller than the width of the flaps 24 at their juncture with the central extent 16, as described above, the flaps 24 may be more securely retained therein by forming a notch or otherwise nicking the flaps 24 at their juncture with the central extent 16 thereby allowing the narrower-width edges of the pocket openings to engage therein. It is also noted that to minimize astigmitation due to swelling, the pockets 46 may be cut further interiorally as shown in FIG. 3A.

In addition to the eye with a repaired cornea and the method of repairing a cornea as set forth above, the present invention also includes a trephine 52.

The trephine 52 of the present invention is particularly useful in cutting and forming the donor material 14 as described above. The trephine 52 of the present invention is for the cutting of donor material 14 and is adapted to be used in corneal transplants. The trephine 52 comprises, in combination, a cylindrical support 56, a plurality of circular cutting blades 58 and 60, radially extending blades 62 and an associated block 64.

More specifically, the cylindrical support 56 of the present invention is adapted to be held by a surgeon in the cutting of the donor material 14. The trephine 52 includes a cylindrical central portion 68 with an upper edge 70 and a lower edge 72. A central axis 74 extends along the length of the cylindrical support 56.

A plurality of circular cutting blades 58 and 60 are formed in the lower edge of the cylindrical support 56. The circular cutting blades 58 and 60 include an exterior continuous cutting blade 74. Such blade has a diameter between about 11 and 12 millimeters. The cutting blades 58 and 60 also include an interior discontinuous cutting blade 76. Such blade has a diameter of about between 7 and 7½ millimeters.

The radially extending blades 62 are located between the circular blades 58 and 60. The exterior circular blade 60 is located closer to the upper edge of the cylindrical support 56 than the interior circular blade 58. This is by a distance of about 100 microns. The radial blades 62 thus extend at an acute angle with respect to the upper edge of the support 56. For producing four flaps, the radial blades 62 are eight in number and arranged as for diamond shaped components. Such components together constitute between about 10 and 100 percent of the circumvents of the inner and outer circular blades 58 and 60. The radially interior edge 96 of the diamond shaped components is blunt to preclude cutting of donor material 14 at such location.

In association with the above trephine 52, there is provided a block 64. Such block 64 has a pocketed, generally spherical surface 80. Such spherical surface has a radius of curvature of about 7.5 millimeters. The purpose of such surface is for constituting a support for the donor material 14 during the cutting thereof by the trephine 52.

The use of the trephine 52 as described above constitutes an inventive method of the present invention in addition to the trephine 52 itself. In practicing the method of cutting donor material 14 with the trephine 52 as described above, the steps include providing a cylindrical support 56 of the type as described above. The method then includes the step of providing a plurality of circular cutting blades 58 and 60 in the cylindrical support 56 as described above. The method also includes the step of providing radially extending blades 62 between the circular blades 58 and 60 as described above. The invention also includes the step of providing an associated block 64 as described above. The method of the present invention then includes the step of positioning donor material 14 adapted to be used in corneal transplants on the support surface 80 of the block 64 and cutting such supported donor material 14 with the trephine 52 as described above.

In the fabrication of the pockets 46 in the recipient eye 10, the incisions which extend generally parallel with the upper and lower surfaces of the eye beneath the Bowman's membrane are preferably done by a conventional diamond knife in the manner described above.

The specifics of the trephine 52 as described above are as follows:

A trephine blade which punches out the donor material to 90 percent of the corneal thickness;

A trephine blade which punches out the donor material at a rim of 10–12 millimeters;

A diamond incision of the superficial Bowman's membrane which fashions corneal flaps for insertion into the recipient rim;

A recipient rim formation beneath the Bowman's membrane of a pocket through which the donor flap is transferred;

The method of securing the donor flap in the recipient rim is with forceps that allow manipulation of the flaps in the postoperative period to reduce the astigmatism and to allow for a spherical surface;

The lack of sutures at the time of corneal transplantation reduces the need for suture adjustment and the attendant micro abscesses and wound compression that occur with all sutures;

The recipient bed is incised in a step fashion to coapt the stroma;

A diamond knife is provided which produces an undermined flap of Bowman's membrane;

A corneal punch which produces donor flaps of Bowman's membrane; and

Forceps for insertion of the Bowman's membrane flaps beneath the recipient rim.

Finally, it is noted that other types of trephines for accomplishing the transplantation method of this invention are currently being researched and developed, which trephines may be the subject of further patent applications directed to such trephines. Further, it is noted that the transplantation method of this invention is not limited to corneal transplantation and may be implemented in other transplantations without departing from the spirit and scope of this invention.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and methods and the combination and arrangement of parts and method steps may be resorted to without departing from the spirit and scope of the invention.

Now that the invention has been described,

What is claimed is:

1. A method of repairing a cornea comprising:

providing a donor material in the shape of a partial sphere having a generally central extent, the central extent being of the size and shape of the central portion of a cornea of an eye, the central extent having a periphery with an exterior surface of a Bowman's membrane in a convex configuration and an interior surface in a concave configuration and with an essentially common thickness throughout, the exterior surface of the central extent having one or more corneal flaps extending radially from the periphery of the central extent, the flaps having exterior surfaces of the Bowman's membrane as a continuation of the exterior surface of the Bowman's membrane of the central extent; and providing a recipient eye in the shape of a partial sphere having a central aperture in the cornea, the central aperture being of a size and shape essentially that of the periphery of the central extent of the donor material, the central portion having pockets and with the central extent of the donor material located within the central aperture of the recipient eye and with the flaps of the central extent being located within the pockets of the recipient eye; and positioning the central extent of the donor material within the aperture of the recipient eye with the flaps of the central extent being located within the pockets of the recipient eye.

* * * * *